United States Patent [19]

Boehringer et al.

[11] Patent Number: 5,120,305
[45] Date of Patent: Jun. 9, 1992

[54] METHOD AND APPARATUS FOR DELIVERING OR WITHDRAWING FLUIDS

[75] Inventors: John R. Boehringer, Wynnewood; John Karpowicz, Glenmoore; David R. Smith, Wayne; Christopher L. Bove, Broomall, all of Pa.

[73] Assignee: Boehringer Laboratories, Norristown, Pa.

[21] Appl. No.: 522,381

[22] Filed: May 11, 1990

[51] Int. Cl.⁵ .................................................. A61M 1/00
[52] U.S. Cl. .......................... 604/35; 604/43; 604/45; 604/49
[58] Field of Search .................. 604/49, 52, 53, 31, 604/35, 43, 45, 317

[56] References Cited

U.S. PATENT DOCUMENTS

| | | | |
|---|---|---|---|
| 4,299,221 | 11/1981 | Phillips et al. | 604/45 X |
| 4,451,252 | 5/1984 | Martin | 604/43 |
| 4,708,717 | 11/1987 | Deane et al. | 604/35 |
| 4,767,417 | 8/1988 | Boehringer et al. | 604/31 |
| 4,781,707 | 11/1988 | Boehringer et al. | 604/317 |

OTHER PUBLICATIONS

Item 1 represents commerical literature showing a prior art suction tube having tips of several configurations (p. 39) date unknown.

*Primary Examiner*—William H. Grieb
*Attorney, Agent, or Firm*—Paul & Paul

[57] ABSTRACT

A method and apparatus is provided for delivering and/or withdrawing fluids. For example, blood may be salvaged from a body cavity of a patient, in which a wand is provided having separate conduits for fluids. Means, for example a valve, is provided for opening or closing the desired conduits, depending upon whether the fluid is to be salvaged or lost to waste, sampled or returned directly to circulation. The apparatus is adapted for surgical use, and most particularly when a partial vacuum is drawn through the conduits, such that operation of the valve can exert a partial vacuum on one or more of the conduits. The entry ends of the conduits are disposed adjacent each other, with the conduits being joined as a wand. The valve is adapted for being actuated upon being held in the hand of the operator. For example, salvage of blood can be collected for autotransfusion to the patient directly, waste irrigants can be collected for disposal, blood or other fluids can be sampled for analysis or blood can be collected to a processing system for subsequent infusion.

When it is desired to deliver fluids, they may be delivered through one or more conduits or lumens and, if desired, removed virtually simultaneously through one or more other conduits or lumens.

39 Claims, 1 Drawing Sheet

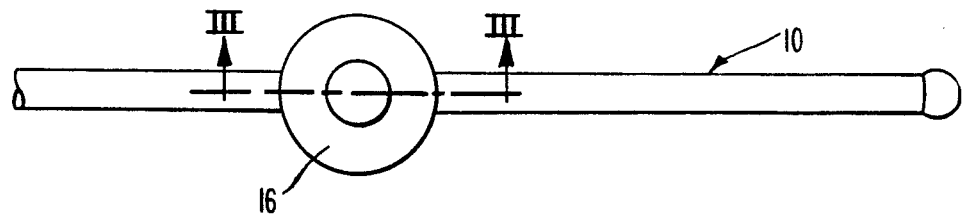
Fig. 1
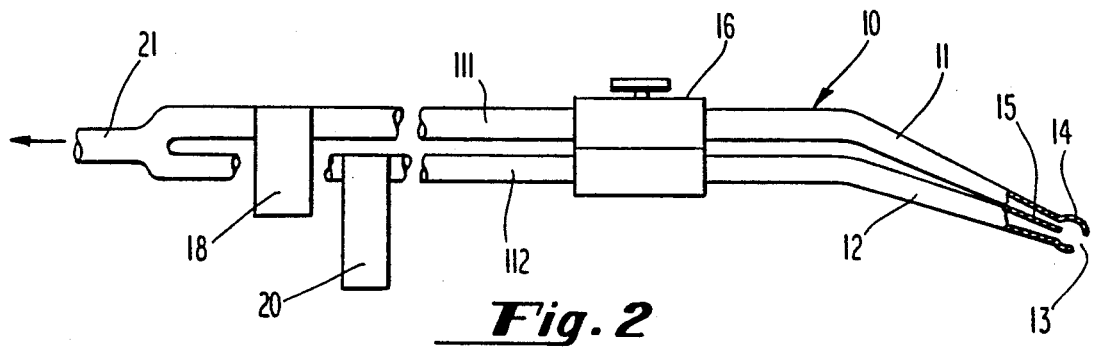
Fig. 2
Fig. 3
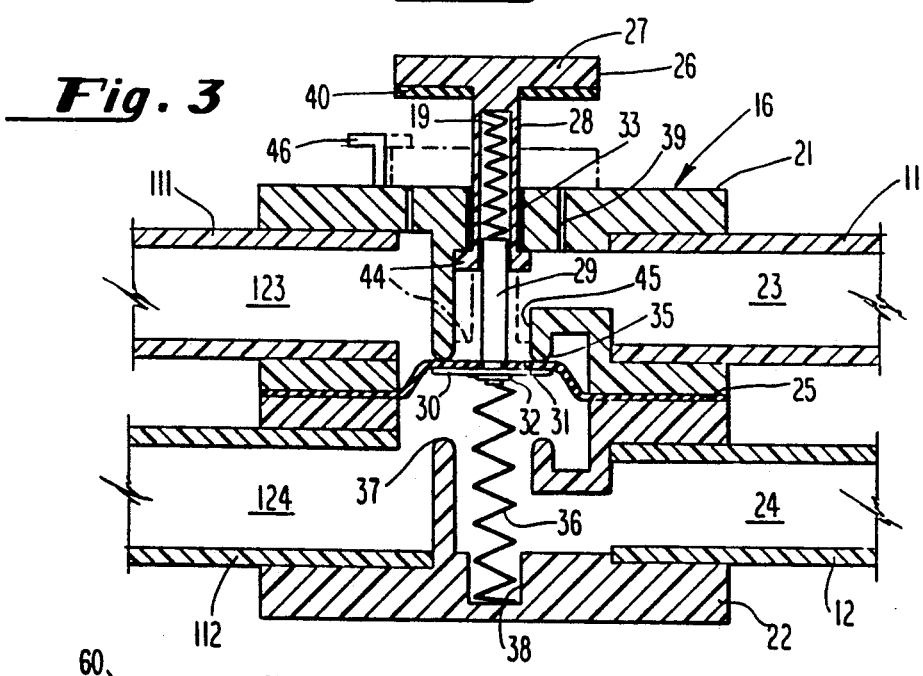
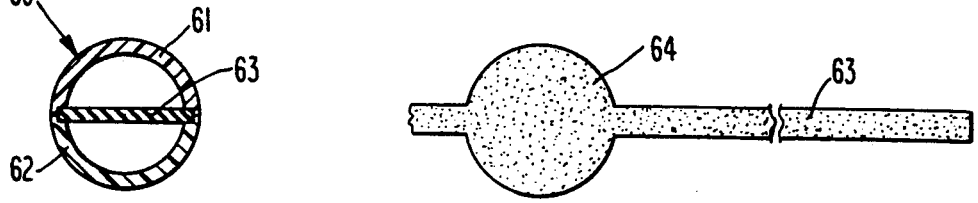
Fig. 4
Fig. 5

METHOD AND APPARATUS FOR DELIVERING OR WITHDRAWING FLUIDS

BACKGROUND OF THE INVENTION

During surgery of mammals, such as human beings, it is commonplace during an operation to draw blood or other fluids from a body cavity, in order to provide visibility to the surgeon and others, or for autotransfusion or for any of various reasons. Typically, the blood being drawn off is drawn via a suction tube, with suction provided generally by means of a source of vacuum that is present in the operating room, and which is used to draw the blood into a collection device. The conduit through which the blood is drawn from the body cavity may be a tube, or wand, as is desired, operated by medical personnel at the site of operation. One such suction draw or drainage device is that set forth in U.S. Pat. No. 4,767,417.

With increased tendency to seek to salvage the blood of a patient during surgery, for re-transfusion or autotransfusion back to the patient, systems have been developed to collect blood for re-use. The advent of processing systems and the like have led to increased clutter in the surgical field, which can lead to inadvertent misapplication of systems and to loss of efficiency. Autotransfusion of collected blood can be substantially immediate, or can be for collection for later retransfusion, as desired. One such process and apparatus for collecting blood for autotransfusion is that set forth in U.S. Pat. No. 4,781,707.

In some instances, such as during surgery, the blood that is collected is a mixture of blood that is readily adapted for reuse or autotransfusion, and blood containing undesirable substances, such as bone chips, irrigating fluids, pharmaceuticals, infectious substances and the like.

Sometimes, the attendant at the site of the operation can instantly observe and distinguish between salvageable, or uncontaminated blood on the one hand, and contaminated or waste blood on the other. In all cases, it is imperative that the surgeon's working field be kept clear and that time not be lost in shifting wands into and out of a cluttered field. Furthermore, it is important that when salvageable fluids, such as blood, are being withdrawn, and especially when it is desired to select between salvageable fluids and non-salvageable fluids, that the two fluids not come into contact with each other.

THE PRESENT INVENTION

The present invention is directed toward a process and device which enables the nurse or other medical attendant, with a single wand or tool, to deliver and/or evacuate blood or other fluid. The present invention provides an efficient system for handling blood whether it is contaminated or uncontaminated, in being able to substantially instantaneously divert salvageable blood to salvage, separating it from contaminated blood, which is to be drawn off and discharged to waste.

SUMMARY OF INVENTION

The present invention is directed to a method and apparatus for delivering and/or collecting fluids to or from a body cavity of a patient and lends itself to use for partial salvage, in which a multiple conduit wand is provided, with a means for valving between the conduits depending upon whether the fluid is being delivered or withdrawn, or when the fluid is blood drawn from a the patient, depending upon whether that fluid is waste or salvage blood.

In this connection, the valve is a readily actuable valve adapted to be actuated by the same hand that holds the apparatus at the site of operation, whereby simple valve actuation can deflect the fluid among conduits.

Accordingly, it is the primary object of this invention to provide a novel method and apparatus for delivering or collecting fluids relative to a body cavity of a patient.

It is a further object of this invention to provide a novel method and apparatus for collecting salvageable blood by segregating it from waste blood at the site of an operation.

It is another object of this invention to provide a novel method and apparatus for collecting other salvageable fluids from waste fluids at the site of an operation.

It is a further object of this invention to accomplish the above object by the use of a tool having blood inlet means closely disposed to a valve which deflects blood to one conduit or the other, depending upon whether it is salvage blood or waste blood.

It is another object of this invention to accomplish the foregoing objects where the valve is normally closed to one conduit, but readily openable relative thereto.

It is another object of this invention to provide a clog-clearing mechanism in the valve means, on the normally closed side of the valve.

It is another object of this invention to segregate fluids for immediate reinfusion, or for delayed infusion.

It is a further object of this invention to provide a means for collecting fluid samples for analysis.

It is a further object of this invention to accomplish the above objects wherein the wand has separate fluid inlets that are in substantially adjacent relation to each other but separated from one another in the valves to avoid contamination.

Other objects and advantages of the present invention will be readily apparent to those skilled in the art from a reading of the following brief descriptions of the drawing figures, detailed descriptions of the preferred embodiment, and the appended claims.

BRIEF DESCRIPTIONS OF THE DRAWING FIGURES

FIG. 1 is a fragmentary top plan view of the apparatus of this invention, illustrating a wand adapted to be hand held, with the valve and its actuator readily illustrated.

FIG. 2 is a fragmentary front elevational view of the wand of FIG. 1, partially broken away to illustrate the interior of the conduit inlet zone for purposes of clarity, and with fluid collection containers for delivering or receiving fluid to or from the wand conduits, also being shown.

FIG. 3 is an enlarged vertical sectional view, taken through the valve illustrated in FIG. 1, generally along the line III—III of FIG. 1, and wherein the inlet and outlet conduits to the valve and the operational components of the valve are most clearly illustrated.

FIG. 4 is a transverse sectional view taken through an alternative multiple-conduit apparatus in accordance with this invention.

FIG. 5 is a schematic view of an alternative integral diaphragm/conduit separator arrangement, for use with an apparatus of the type of FIG. 4.

DESCRIPTION OF THE PREFERRED EMBODIMENT

Referring to the drawings now in detail, reference is first made to FIG. 1, wherein the fluid delivery/collection wand 10 is illustrated as comprising a first conduit 11 for collecting fluid, and a second conduit 12, having a common inlet 13 in a conjoined inlet head 14, with the inlet being separated by a separator wall 15 just inboard of the opening 13.

A valve 16 is shown for deflecting fluid from a patient that is received via inlet 13, and which enters one of the conduits 11 or 12, depending upon which conduit is open, to one of conduits 111, 112, generally to a salvage container 18, or a waste container 20, as desired. Generally, separate vacuum sources will be connected to the conduits 111, 112, via vacuum lines 21a and 21b.

Alternatively, the valve 16 can be used to deliver fluid to a patient, in which the fluid may be provided under a source of pressure provided on the line 21, such as air pressure, that may deliver rinse liquid, saline, pharmaceuticals, irrigation fluid or other fluids. Such fluid will be impelled from one or more of the containers 18, 20, to be delivered to the valve 16, to then be deflected to discharge at 13, via one or more conduits 11, 12, whereby a patient wound or the like may be treated.

Even further, one fluid may be delivered to a wound, for example, from container 20 or otherwise, into one of the left-most conduit portions 112 illustrated in FIG. 2, through valve 16, and into conduit portion 12, alternating with evacuation of that and/or other fluid via line 11, through valve 16, via line 111, via one of vacuum draw-off lines 21a, 21b, if desired. In this arrangement, a single wand can both deliver and evacuate fluids, alternating from one to the other, as desired. In such an arrangement the vacuum draw-off line 21a would not be fluid-flow connected to line 112, but would be connected to a fluid delivery line 111.

The collector 18 may if desired be constructed along the lines of the collection chamber for autotransfusion use that is disclosed in U.S. Pat. No. 4,781,707, or may take other forms. In such a case, the vacuum from line 21 may be directly applied to the collection chamber 18, as shown, or such may be provided through a fluid control chamber.

The waste collection chamber 20 may, if desired be constructed as one of the chambers shown in the apparatus of U.S. Pat. No. 4,767,417, if desired, or such may take other forms. It will also be understood that, if desired, the discharge of waste blood may be to some form of discharge other than a collection chamber.

With specific reference to the valve 16, best illustrated in FIG.3, it will be seen that the valve 16 includes upper and lower housing members 21 and 22 respectively, which receive therein inlet and outlet conduits 11, 12, 111, 112, respectively, as shown, suitably fitted into openings such as 23, 24, 123, 124 at the inlet and outlet ends of the valve housings 21 and 22, respectively. It will be understood that the fitting of conduits into the openings of the valves will preferably be airtight, and such may be merely tight fittings, or may be solvent sealed or heat sealed therein. Similarly, the housing members 21, 22 may be fastened together by any suitable means, such as bolts (not shown) heat sealed, etc., it only being necessary that the housing members be suitably secured together.

A diaphragm 25 of a suitable elastomeric material, flexible to permit movement between valving positions, is provided, disposed in sandwiched relation between the housing members 21, 22, as shown.

A valve operator or actuator 26 is provided, having an upper hand or finger actuatable button 27, and a hollow depending stem 28, slidably receiving a post 29 therein. Beneath the post 29 a suitable washer 30 is carried, for engaging the central portion 31 of the diaphragm between the bottom of the post 29 and the washer 30. The lower-most end 32 of the post 29 has a suitable pin or like member extending therethrough, to hold the washer 30 in place. A compression spring 19 is carried in the stem 28 for urging the button 27 upwardly relative to the post 29. The stem 28 is provided with clearance 33 through the housing 21. The clearance hole 33 operates as a vent for the right side of the valve of FIG. 3 in the salvage mode of fluid recovery.

Another vent 34 is provided in the upper end of the housing 21, in the zone of the salvage conduit 111 to enable the negative pressure above the diaphragm inside the outlet zone of the salvage mode conduit 111 to remain substantially atmospheric so as not to inhibit opening of the valve when the actuator 26 is depressed to cause the diaphragm 31 to be unseated relative to the seating port 35. It will be understood that the seating port 35 has a cylindrical opening that is normally closed by the diaphragm 31, as shown, but that, upon depressing the actuator 26, against the force exerted by a compression spring 36 (or by inherent resilient bias built into the diaphragm 31), such that the preferably elastomeric sealing washer 30 is urged downwardly to seat against the cylindrical port 37, the conduit 12, 112 will be closed from inlet to outlet, and the salvage conduit 11, 111 will be open from inlet to outlet, for flow of blood or other fluid through the then open port 35. For facilitating proper seating of the compression spring 36, a blind bore 38 is provided in the housing member 22, and at the upper end of the spring 36, the spring may seat over the depending portion 32 of the port 29, as shown. Thus, depression/raising of the actuator 26 effects a sequenced opening/closing of the conduit 11, 111 and a closing/opening of the conduit 12, 112, in automatic fashion.

Still another vent 39 is provided, likewise beneath the head 27 of the button 26, to vent line 11, or conduit 23. This is particularly desirable when the diaphragm is closed in the position as shown in FIG. 3, such that fluids in the conduit zone 23 may drain back to the patient, rather than remaining in the conduit zone 23 when the button is in the position illustrated. Then, as for example, when blood or other fluid is to be drawn through line 23, to be delivered to conduit zone 123, and the button 26 is pushed downwardly to open the valve between conduit zones 23 and 123, the seal 40 beneath the button 27 may close the vent 39, so that air and blood (if blood is the fluid being drawn) are not aspirated at the same time. It is desirable to avoid aspirating air and blood, to avoid foaming and/or hemolysis.

For proper operation of the valve 16, the spring 19 will be a lower tension spring than the spring 36, such that when the button 27 is depressed, the spring 19 will be compressed first, or prior to the spring 36 being compressed, such that the stem 28 will slide down over the post 29 such that the anti-clogging disk 44, carried at the lower end of stem 28, may ride downwardly over the post 29, to slide over and wipe the surface 45 of valve port 35, to prevent build-up of fluid and clotting at that location. In this regard, the anti-clogging disk 44 is shown in a phantom position at the bottom of the port 35. An alternative or supplementing anti-clogging means may be provided in the form of a coating of a clot-resistant formulation on the interior of the valve and/or one or more of the conduits.

When the button 27 is pushed downwardly to the phantom line position therefore illustrated in FIG. 3, a hold-down device or latching means 46, carried on the housing 21 may be rotated from the full line position therefore illustrated in FIG. 3, to the phantom line position illustrated therefore, overlying and holding the head of the button 27 in its downward position. This will allow a hands-off operation of the valve, if desired.

It will further be understood that the venting of the lines allows a fluid to move advantageously. In instances when the fluid is blood, it may be moved to the reservoir in such a way that clotting is minimized. Furthermore, the venting may clear portions of the wand of dormant fluids, such as blood.

It will also be noted that beneath the head 27 of the actuator 26, the elastomeric seal 40 is provided to facilitate a sealed closing of all of the vents 34, 39 and the vent at the enlarged opening 33, upon depression of the actuator 26.

It will thus be seen that what is presented is a efficient means for automatically venting when needed, and discontinuing the venting when needed, depending upon whether or not the actuator or plunger 27 is depressed.

It will further be seen that the surgeon, nurse, or other operating room professional can readily and instantaneously determine whether blood or other fluid that is to be withdrawn from a cavity of a patient is blood that is suitable for salvage or not, and if so, may, upon holding the wand 10 in hand, simply depress the plunger 27, which will substantially instantaneously allow the vacuum source connected via tubing or the like 21, to be drawn off the left side of the conduit 111, whereby blood may enter the upper portion of the inlet 13, for substantially immediate entry into the conduit 11, for delivery to collection chamber 18. Similarly, if the professional attendant should notice that blood or other fluid approaching the inlet 13 appears to be contaminated fluid, the actuator 27 may be released, such that it will be spring-biased upwardly, substantially immediately, whereupon the diaphragm 31 may again close the port 35, such that fluid that is desired to be passed to waste, will enter the conduit 12 for delivery via conduit 112 to a waste receptacle 20 or the like.

It will be apparent from the foregoing that the placement of the valve 16 along the conduits 11 and 12 may be varied as a matter of convenience. It will further be apparent that the wand inlet 13 is bifurcated at 11, 12 by means of the separator 15, as close as possible to the situs of the inlet 13, (assuming operation in a withdrawal mode whereby 13 functions as an inlet) such that the actual inlets to the conduits 11 and 12 will be as close as possible to the wand inlet opening 13, but that some variation may be desired. For example, if the valve 16 is placed close to the wand inlet opening 13, it may be possible to replace the separate conduits on the inlet side of the valve 16, with a single conduit, although such would not be preferable because the amount of fluid in that portion of the conduit should first be purged before diverting the fluid from waste to salvage.

Accordingly, it is a preferred embodiment of this invention that the inlets to each of the conduits be substantially completely separate, as shown, although adjacent to each other. An alternative construction for multiple conduits could comprise a single conduit 60 divided throughout its length into a plurality of conduit portions 61, 62, separated from communication with each other by a separator 63. The separator 63 could be rubberlike, if desired, and could also be integral with the diaphragm 31, as in FIG. 5. In FIG. 5 the separator 63 is integral with the diaphragm 64, which, in turn, is constructed like the diaphragm 31.

From the foregoing, it will be apparent that fluids may be drawn from a body cavity, into one of the other conduits of a wand, such that the operator may selectively cause the fluid to be delivered one place or the other; such as for salvage or for discharge. Alternatively, incoming fluids, such as irrigation fluid may be delivered through one of the conduits, and then, upon actuation of the valve, that fluid or a different fluid may be withdrawn through another of the conduits.

The wand of the present invention may also provide a means for alternating between types of fluids that are being delivered to a patient.

It will also be understood that various modifications of each of these uses, as well as combinations of them, may be made. For example, while two basic conduits are shown for the valve of the present invention, it will be understood that more than two conduits may be utilized, for introduction of a plurality of different fluids through different conduits alternately with the drawing-off of fluids from other conduits, or even simultaneously therewith, as desired.

It will further be noted that the components of this invention will be constructed to be suitable plastics, tubing, and the like, and of materials that are known and adaptable for medical uses.

Various changes may, however, be made in the details of construction, as well as in the use and operation of the apparatus and the method of the present invention, all within the spirit and scope of the invention, as recited in the appended claims.

What is claimed is:

1. A method of collecting blood from a body cavity of a patient for partial salvage, comprising the steps of:
  (a) providing a dual conduit wand having blood inlet for the conduits for receipt of blood from a patient;
  (b) providing a valve between the conduits for alternately opening the one conduit to waste while the other conduit is closed to salvage and the converse;
  (c) drawing partial vacuums on both conduits of the wand;
  (d) placing an end of the wand having blood inlets thereat in a body cavity of a patient; and
  (e) selectively opening the valve between the two conduits to withdraw waste blood through a waste-carrying conduit for deposit to blood waste while closing the valve to a salvage-carrying conduit; and then alternately opening the valve to withdraw salvage blood through a salvage-carrying conduit for deposit to blood salvage.

2. A method of fluid transfer relative to a body cavity of a patient, comprising the steps of:
  (a) providing a multiple conduit wand having at least first and second fluid transfer conduits for handling fluid relative to a patient;
  (b) providing a valve between the conduits for alternately opening at least a first conduit while maintaining at least a second conduit closed, and the converse;

(c) providing a source of fluid flow on at least one conduit of the wand;

(d) placing an end of the wand having fluid opening(s) to the conduits in a body cavity of a patient; and (e) selectively operating the valve between the conduits to transfer fluid through the first conduit while closing the valve to the second conduit, and then alternately opening the valve to transfer fluid through the second conduit while closing the valve to the first conduit.

3. The method of claim 2, wherein the selective operating step includes transferring fluid received into a fluid opening alternately through the first and second conduits, depending upon the open position of the valve relative to a conduit.

4. The method of claim 2, wherein the selective operating step includes alternately transferring fluid through the first and second conduits and out through a fluid opening depending upon the open position of the valve relative to a conduit.

5. The method of claim 2, wherein the selective operating step includes alternately delivering o withdrawing fluid through the first and second conduits, depending upon the open position of the valve relative to a conduit.

6. The method of any one of claims 1-5, wherein the wand that is provided, provides inlets to the conduits in substantially adjacent relationship to each other.

7. The method of claim 1, wherein the wand that is provided, provides inlets to the conduits in substantially adjacent relationship to each other; wherein the step of selectively opening the valve includes the step of maintaining the valve normally closed across one conduit and normally open across the other conduit.

8. The method of claim 6, including the step of venting the closed conduit and discontinuing the venting to a conduit when the conduit is open.

9. The method of claim 1, wherein the wand that is provided, provides inlets to the conduits in substantially adjacent relationship to each other; wherein the step of selectively opening the valve includes the step of maintaining the valve normally closed across one conduit and normally open across the other conduit, wherein the step of maintaining the valve includes keeping the valve normally closed across the salvage-carrying conduit and normally open across the waste-carrying conduit.

10. The method of claim 7, wherein the maintaining step includes spring-biasing the valve in one position.

11. The method of claim 8, wherein the step of discontinuing the venting occurs automatically in response to opening the valve.

12. The method of claim 1, wherein the wand that is provided, provides inlets to the conduits in substantially adjacent relationship to each other; including the steps of depositing waste blood in a waste receptacle and depositing salvage blood in a salvage receptacle.

13. The method of claim 6, wherein the steps of opening and closing the valve includes moving a flexible diaphragm away from and toward valve closure ports, respectively.

14. The method of any one of claims 1-5, including the step of wiping a portion of the valve with an anti-clogging device to prevent valve clogging.

15. The method of claim 1, wherein the wand that is provided, provides inlets to the conduits in substantially adjacent relationship to each other; wherein the step of selectively opening the valve includes the step of maintaining the valve normally closed across one conduit and normally open across the other conduit, including the step of venting the closed conduit and discontinuing the venting to a conduit when the conduit is open, wherein the step of maintaining the valve includes maintaining the valve normally closed across the salvage-carrying conduit and normally open across the waste-carrying conduit, wherein the maintaining step includes spring-biasing the valve in one position, including the step of wiping a portion of the valve with an anti-clogging device to prevent valve clogging, wherein the step of discontinuing the venting occurs automatically in response to opening the valve, including the steps of depositing waste blood in a waste receptacle and depositing salvage blood in a salvage receptacle; wherein the steps of opening and closing the valve includes moving a flexible diaphragm away from and toward valve closure ports, respectively.

16. Apparatus for collecting blood from a body cavity of a patient for partial salvage, comprising:

(a) a wand having dual conduits, with inlet means for receipt of blood from a patient;

(b) valve means between the conduits for alternately opening the one conduit to waste while the other conduit is closed to salvage and the converse;

(c) means for connection to a source of partial vacuum on both conduits;

(d) one end of the wand having opening means thereat for receiving blood therein upon being placed in a body cavity of a patient; and (e) means for selectively opening the valve means between the two conduits to withdraw waste blood through a waste-carrying conduit for deposit to waste while closing the valve means to a salvage-carrying conduit and then alternately opening the valve means to withdraw salvage blood through a salvage-carrying conduit for deposit to blood salvage.

17. Apparatus for fluid transfer relative to a body cavity of a patient, comprising:

(a) a multiple conduit wand having at least first and second fluid transfer conduits for handling fluid relative to a patient;

(b) valve means between the conduits for alternately opening at least a first conduit while maintaining at least a second conduit closed, and the converse;

(c) means for connection to a source of fluid flow on at least one conduit of the wand;

(d) one end of the wand having fluid opening means thereat for fluid transfer relative to a body cavity of a patient; and (e) means for selectively operating the valve means between the conduits to transfer fluid through the first conduit while closing the valve means to the second conduit, and then alternately opening the valve means to transfer fluid through the second conduit while closing the valve means to the first conduit.

18. The apparatus of claim 17, wherein the means for selectively operating includes means for transferring fluid received into a fluid opening alternately through the first and second conduits, depending upon the open position of the valve relative to a conduit.

19. The apparatus of claim 17, wherein the means for selectively operating includes means for alternately transferring fluid through the first and second conduits and out through a fluid opening depending upon the open position of the valve relative to a conduit.

20. The apparatus of claim 17, wherein the means for selectively operating includes means for alternately delivering or withdrawing fluid through the first and second conduits, depending upon the open position of the valve relative to a conduit.

21. The apparatus of any of claims 16–20, wherein said opening means comprise substantially separate inlets in substantially adjacent relationship to each other.

22. The apparatus of claim 16, wherein said opening means comprise substantially separate inlets in substantially adjacent relationship to each other, wherein the means for selectively opening the valve means includes means maintaining the valve means normally closed across one conduit and normally open across the other conduit.

23. The apparatus of claim 21, including means venting a closed conduit and discontinuing the venting to a conduit when the conduit is open.

24. The apparatus of claim 16, wherein said opening means comprise substantially separate inlets in substantially adjacent relationship to each other, wherein the means for selectively opening the valve means includes means maintaining the valve means normally closed across one conduit and normally open across the other conduit, wherein means maintaining the valve includes means keeping the valve means normally closed across the salvage-carrying conduit and normally open across the waste-carrying conduit.

25. The apparatus of claim 22, wherein the means maintaining the valve includes means spring-biasing the valve in one position.

26. The apparatus of claim 23, wherein the means for discontinuing the venting includes means for automatically doing so in response to opening the valve means.

27. The apparatus of claim 16, wherein said opening means comprise substantially separate inlets in substantially adjacent relationship to each other; including a waste receptacle and a salvage receptacle, means connecting the waste-carrying conduit to the waste receptacle for depositing waste blood therein, and means connecting the salvage-carrying conduit to the salvage receptacle for depositing salvage blood therein.

28. The apparatus of claim 21, wherein the means for opening and closing the valve means includes a flexible diaphragm and valve closure ports, and means for moving the diaphragm away from and toward valve closure ports, respectively.

29. The apparatus of any one of claims 16–20, including means for preventing clogging of the valve means by wiping a portion of the valve means with an anti-clogging device.

30. The apparatus of claim 16, wherein said opening means comprise substantially separate inlets in substantially adjacent relationship to each other, wherein the means for selectively opening the valve means includes means maintaining the valve means normally closed across one conduit and normally open across the other conduit, including means venting a closed conduit and discontinuing the venting to a conduit when the conduit is open, wherein the means maintaining the valve means includes means keeping the valve means normally closed across the salvage-carrying conduit and normally open across the waste-carrying conduit, wherein the means maintaining the valve means includes means spring-biasing the valve means in one position, wherein the means discontinuing the venting includes means for automatically doing so in response to opening the valve, including means for preventing clogging of the valve means by wiping a portion of the valve means with an anti-clogging device; including a waste receptacle and a salvage receptacle, means connecting the waste-carrying conduit to the waste receptacle for depositing waste blood therein, and means connecting the salvage-carrying conduit to the salvage receptacle for depositing salvage blood therein; wherein the means for opening and closing the valve means includes a flexible diaphragm and valve closure ports, and means for moving the diaphragm away from and toward valve closure ports, respectively.

31. Apparatus according to claim 17, including means for connection to a source of vacuum, on at least one of the conduits.

32. Apparatus according to claim 17, including means for connection to at least one source of positive pressure fluid on at least one conduit.

33. Apparatus according to claim 31, including sequencing means to open or close at least one conduit as another conduit is closed or opened.

34. Apparatus according to claim 17, including latching means to hold at least one conduit in an opened or closed position.

35. Apparatus according to claim 17, wherein said valve means includes anti-clogging means for clog prevention.

36. Apparatus according to claim 17, wherein said valve means includes a diaphragm.

37. Apparatus according to claim 17, wherein said multiple conduits comprise multiple portions of a single conduit, said portions being separated from communication with each other along their length by separation means traversing the length of the conduit.

38. Apparatus according to claim 37, wherein said valve means includes a diaphragm, and wherein said diaphragm and separation means are integral with each other.

39. Apparatus according to claim 17, including means providing a coating on an inner surface of at least one said conduit, with said coating means comprising an anti-clotting substance.

* * * * *